(12) United States Patent
Methot

(10) Patent No.: US 8,423,335 B2
(45) Date of Patent: Apr. 16, 2013

(54) DENTAL ANALYSIS METHOD AND SYSTEM

(76) Inventor: Alain Methot, Quebec (CA)

( * ) Notice: Subject to any disclaimer, the term of this patent is extended or adjusted under 35 U.S.C. 154(b) by 0 days.

(21) Appl. No.: 13/267,615

(22) Filed: Oct. 6, 2011

(65) Prior Publication Data

US 2012/0185217 A1    Jul. 19, 2012

Related U.S. Application Data

(63) Continuation of application No. 11/990,661, filed as application No. PCT/CA2006/001374 on Aug. 21, 2006, now abandoned.

(60) Provisional application No. 60/748,196, filed on Dec. 8, 2005, provisional application No. 60/709,460, filed on Aug. 19, 2005.

(51) Int. Cl.
*G06G 7/48* (2006.01)

(52) U.S. Cl.
USPC .............................................................. 703/6

(58) Field of Classification Search .................. 703/6
See application file for complete search history.

(56) References Cited

U.S. PATENT DOCUMENTS

| | | | |
|---|---|---|---|
| 4,416,063 A * | 11/1983 | Nestor et al. | 33/810 |
| 5,659,625 A | 8/1997 | Marquardt | |
| 5,867,588 A | 2/1999 | Marquardt | |
| 6,261,248 B1 | 7/2001 | Takaishi | |
| 6,413,085 B1 | 7/2002 | Lee | |
| 6,821,116 B2 | 11/2004 | Severance | |
| 7,833,013 B2 * | 11/2010 | Diers et al. | 433/72 |
| 2005/0043837 A1 | 2/2005 | Rubbert et al. | |

FOREIGN PATENT DOCUMENTS

CA    2346299 A1    4/2000

OTHER PUBLICATIONS

Wards; "Proportional Smile Design Using the Recurring Esthetic Dental (RED) Proportion", Dental Clinics of North America; Jan. 2001; pp. 143-154.

* cited by examiner

*Primary Examiner* — Hugh Jones

(57) ABSTRACT

A dental analysis system and method for designing the dentition of a patient, comprising the steps of: providing a visual representation of the dentition, inputting a value representative of the number of teeth on a side of the dentition, inputting at least two quantities taken from a group consisting of a ratio, an inter-teeth distance and a central incisor width, computing the position of the teeth within the dentition by applying a mathematical function to the value representative of the number of teeth on a side of the dentition and at least two quantities and juxtaposing positioning lines over the visual representation of the dentition, the positioning lines indicating the position of the teeth as computed.

23 Claims, 13 Drawing Sheets

DENTAL ANALYSIS METHOD AND SYSTEM

CROSS-REFERENCE TO RELATED APPLICATION

This is a continuation of U.S. patent application Ser. No. 11/990,661 filed Jan. 16, 2009 now abandoned, which is the national stage of International Application No. PCT/CA2006/001374 filed on Aug. 21, 2006, which claims the benefits of U.S. patent applications No. 60/709,460 filed Aug. 19, 2005 and No. 60/748,196 filed Dec. 8, 2005; which are hereby incorporated by reference.

TECHNICAL FIELD

The present invention relates to a dental analysis method and system. More specifically, the present invention relates to an analysis method and system for the evaluation. planning and modification of the dentition of a patient.

BACKGROUND

In the study of what is considered "beautiful", in nature, human features, architecture, art, etc., it was discovered that there is a common principle at work. This common principle is the universal recognition of pleasant proportions. People have an inherent ability to recognize that an art object has good or bad proportions, or that a person's torso compared to his/her legs looks too long, or too short and out of proportion. This universal common principle thread of proportion, known since antiquity, is referred to the Golden Proportion or Divine Proportion.

Human beauty is also governed by the Golden Proportion. Squares based The Go/den Proportion have been used to define the ideal location of the pupils and outside corners of the mouth. Lines based on the Golden Proportion have been used to define, for example. the ideal positioning of the nose, the tip of the nose. the inside of the nostrils. the two rises of the upper lip. the inner points of the ear, the distance from the upper lip to the bottom of the chin, as well as the width of the nose, the distance between the eyes and eye brows and the distance from the pupils to the tip of the nose.

The Golden Proportion has also been used to study the human dentition. The four front teeth, from central incisor to premolar constitute the most significant part of the dentition and they are in the proportion to each other following the Golden Proportion. This phenomenon has been combined in a grid which may be used to assist in perfecting the aesthetics of the front teeth. However. such grid may be used only for the front four teeth and in some instances the front six teeth but with mitigated results. Accordingly, there is a need for a modified In the present specification, there is described embodiments of a method and system designed to overcome the above-described limitations of the conventional techniques.

SUMMARY

The present invention relates to a method and system for designing the dentition of a patient, comprising the steps of:
inputting a value representative of the number of teeth on each side of the dentition;
inputting at least two quantities taken from a group consisting of a ratio, an inter-molar distance and a central incisor width; and
computing the position of the teeth within the patient's dentition by applying a mathematical function to the value representative of the number of teeth on each side of the dentition and the at least two quantities.

The present invention also relates to a method and system for designing the dentition of a patient, comprising the steps of:
providing a visual representation of the dentition;
inputting a value representative of the number of teeth on a side of the dentition;
inputting at least two quantities taken from a group consisting of a ratio. an inter-teeth distance and a central incisor width;
computing the position of the teeth within the dentition by applying a mathematical function to the value representative of the number of teeth on a side of the dentition and the at least two quantities; and
juxtaposing positioning lines over the visual representation of the dentition, the positioning lines indicating the position of the teeth as computed in step d.

The present invention further relates to a method and system for designing the dentition of a patient as described above, further comprising the steps of adjusting the angle of at least one of the positioning lines.

BRIEF DESCRIPTION OF THE DRAWINGS

A non-limitative illustrative embodiment of the invention will now be described by way of example only with reference to the accompanying drawing, in which.

DETAILED DESCRIPTION

Generally stated, the non-limitative illustrative embodiment of the present invention provides a method and system for the evaluation, planning modification of the dentition of an individual, such as, for example, a patient, by the application of generally vertical lines, hereby referred to as 'positioning lines', following a modified Golden Proportion, which may be determined either explicitly or implicitly from measurements such as, for example, central incisor width and inter-molar distance, onto the dentition of the patient in order to determine 'ideal' positioning of the patient's teeth. In one embodiment, the resulting positioning lines may be applied to 2D or 3D digital images, X-rays, computed tomography (CT) scans, etc., of the patient's dentition or may be included as part of a modeling or re-modeling software to dispose the teeth when creating, for example, ceramic teeth, orthodontic molds, dentures, etc. In a further embodiment, the positioning lines may be angled at a specific angle in order to address an occlusion condition or for aesthetical considerations.

Golden Proportion

Figure 1:
FIG. 1 is a schematic diagram illustrating the Golden Proportion concept.

The Golden Proportion, or Divine Proportion, represents a ratio of 1:1.618. It has been used in a multitude of applications and is well known in the art. Briefly speaking, referring to FIG. 1, the Golden Proportion may be expressed as:

$$\frac{AB}{CB} = \frac{CB}{AC} = 1.618.$$ Equation 1

For example, if the distance AB is 10 mm, then the distance AC will be 3.82 mm and CB will be 6.18 mm.

Dentition

Figure 2:
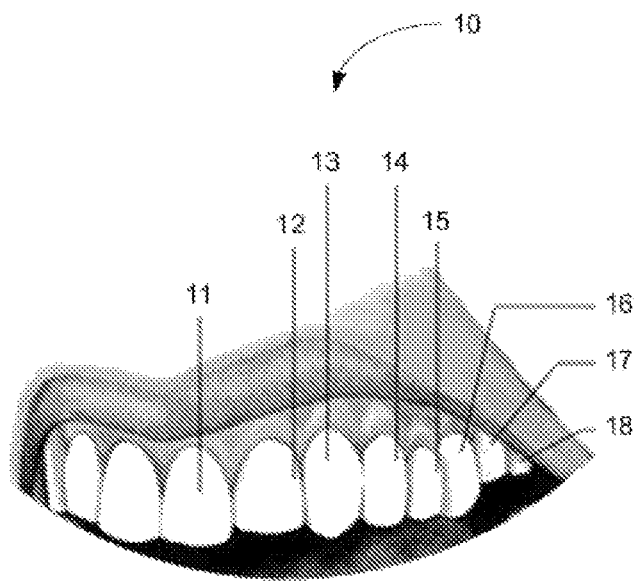
FIG. 2 is a front view illustration of the upper teeth of an individual.

Referring to FIG. 2, the dentition (10) generally comprises the central incisor (11), the lateral incisor (12), the canine (13), the first premolar (14), the second premolar (15) and the first molar (16). The second (17) and third (18) molars are usually not visible in the smile. It is to be understood that for the purpose of clarity FIG. 2 only shows the left side of the dentition (10), the right side being symmetrical.

For the sake of clarity, from thereon reference will be made to the positioning lines on either the left side or the right side of the dentition (10) but it is to be understood that by virtue of symmetry, the same comments apply to the positioning lines on other side of the dentition (10).

Application of the Golden Proportion

Figure 3:
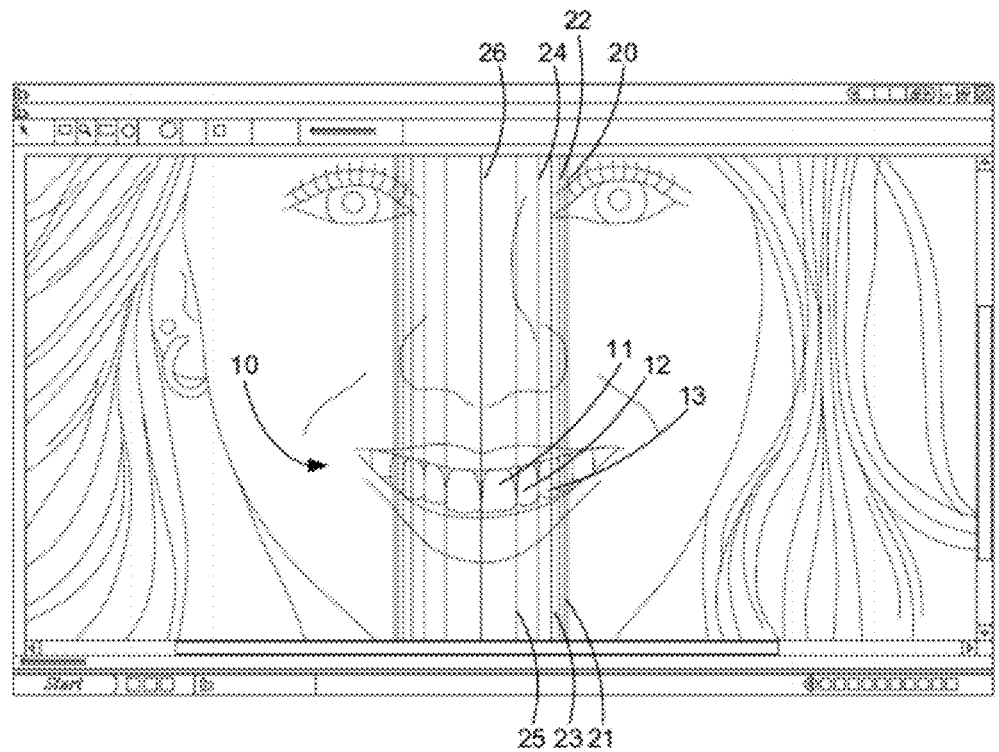
FIG. 3 is a front view image of the smile of an individual on which are superimposed positioning lines following a Golden Proportion with a ration of 1:1.618.

Referring to FIG. 3, there is shown a front view image of a patient's dentition (10) on which is applied the Golden Proportion (ratio of 1:1.618) with seven positioning lines, resulting in a center positioning line (26) and six side positioning lines (25, 24, 23, 22, 21, 210) on one side of the dentition (10). The center positioning line (26) is positioned at the center of the dentition (10) and the last side positioning line (20) is positioned by the user such that the second positioning line (25) is positioned between the central incisor (11) and the lateral incisor (12). Once the first (26) and last positioning lines (20) are positioned, the remaining side positioning lines (25, 24, 23, 22, 21) are computed using the Golden Proportion with a ratio of 1:1.618. As may be seen in FIG. 3, the position of the central incisor (11) and the lateral incisor (12) generally correspond to side positioning lines (25) and (24), respectively, but the position of the canine (13) does not fit with side positioning lines (23), the side positioning line (23 actually passing in the middle of the canine (13).

Application of the Golden Proportion

Figure 4:
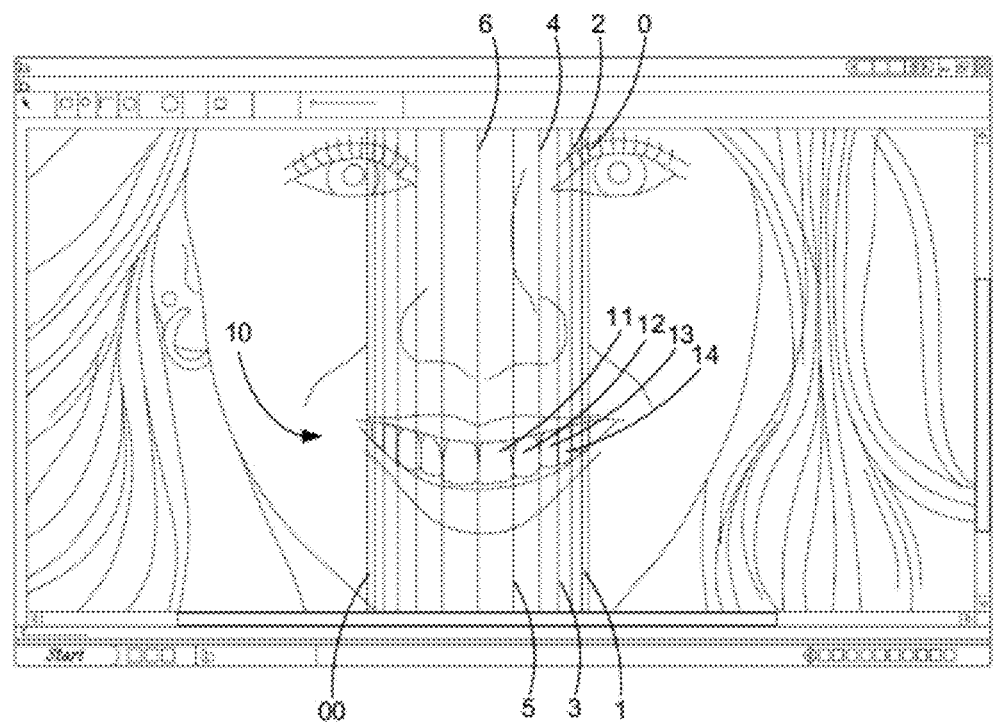
FIG. 4 is a front view image of the smile of an individual on which are superimposed positioning lines following the modified Golden Proportion with a ratio of 1:1.367.

Referring now to FIG. 4, there is shown an image of the patient's smile on which is applied the modified Golden Proportion (ratio of 1:1.367) with seven positioning lines, resulting in a center positioning line (6) and six side positioning lines (5, 4, 3, 2, 1, 0) on one side of the dentition (10). The center positioning line (6) is fixed at the center of the dentition (10) and the last side positioning line (0) is positioned by the user, advantageously on the buccal face of the first molar (16), the remaining side positioning lines (5, 4, 3, 2, 1) being computed using the modified Golden Proportion with a ratio of 1:1.367. As may be seen in FIG. 4, the position of the central incisor (11), the lateral incisor (12), the canine (13) and the first premolar (14) generally correspond to side positioning lines (5), (4), (3), (2), (1) and (0), respectively. Furthermore, referring to FIG. 12, the modified Golden Proportion may be used with a real wax-up of the patient, which in turn is used to create, for example, crowns for the patient. Thus, in this illustrative embodiment, using the modified Golden Proportion, 12 front teeth (six on each side) of the dentition (10) were positioned instead of only four, as seen in FIG. 3. It is to be understood that the same technique described above using seven positioning lines for the positioning of 12 front teeth may also be extended to, for example, nine positioning lines permitting the positioning of 16 teeth. The number of teeth visible in the smile may vary from patient to patient depending on the physiognomy of the patient.

Figure 19:
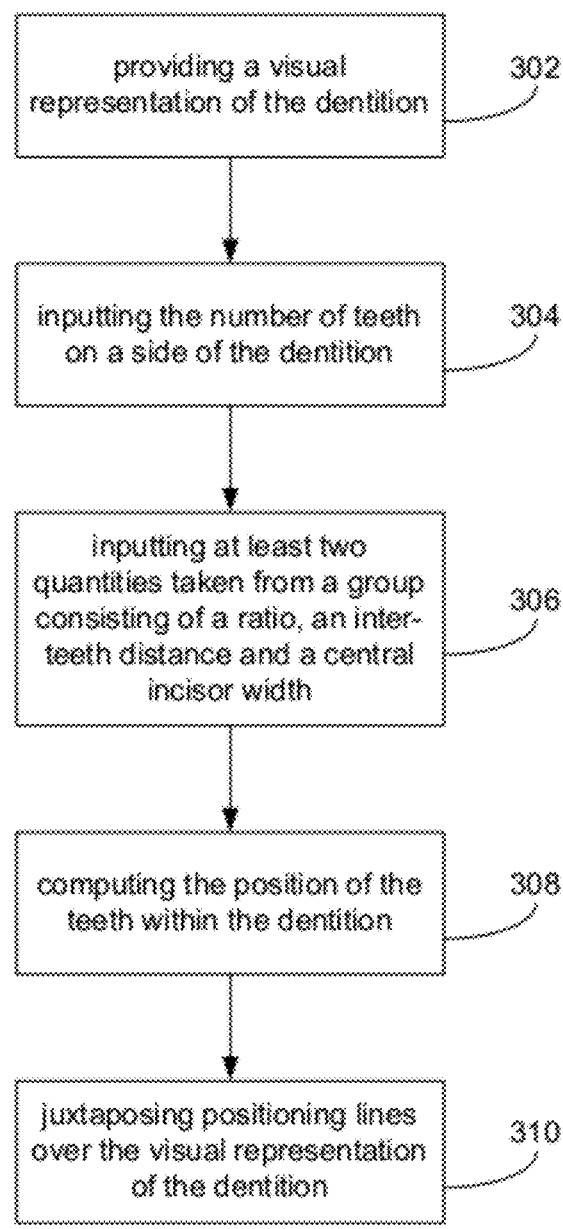
FIG. 19 is a flow diagram depicting the modified Golden Proportion calculator process.

Although in a modified Golden Proportion with a ratio of 1:1.367 was used in FIG. 4, it is to be understood that it may vary depending on the physiognomy of the patient of the desired aesthetical effect. Common ratio values may be, for example, from 1:1.250 to 1:1.500, though more commonly from 1:1.360 and 1:1.400, and with rare occurrence from 1:1.500 and 1:1.618. It should also be understood that when using software tools, such as the modified Golden Proportion calculator which will be introduced further on, the modified Golden Proportion ratio is not limited to three decimals and may vary in precision depending on the application. For example, FIG. 19 shows an interface (200) for a modified Golden Proportion calculator in which the modified Golden Proportion ratio (208) is precise up to 13 decimals, i.e. 1.3676540544138.

Computing the Position of the Side Positioning Lines

As mentioned above, the central positioning line (6) is placed in the center of the smile and dentition (10) and the last side positioning line (0) is positioned by the user, advantageously on the buccal face of the first molar (16), the remaining side positioning lines (5, 4, 3, 2, 1) being computed using the modified Golden Proportion for a given ratio. The side positioning lines (5, 4, 3, 2, 1) may be computed as follows:

$$P(I)=P(i-1)-D/F_i, \ i=0 \text{ to } n-2; \quad \text{Equation 2}$$

where
n is the number of positioning lines;
P(i) is the position of the positioning line (i), i=0 to n−1;
P(0) and P(n−1) are given;
D is the distance between positioning lines (0) and (n−1), i.e. [P(0) and P(n−1)];

$$F_i = \sum_{j=0}^{n-2} R^j; \quad \text{Equation 3}$$

$$F_I=F_{I-1}/R; \text{ and} \quad \text{Equation 4}$$

R is the ratio of the modified Golden Proportion;
which in the context of FIG. 4 translates to:

$$P(1)=P(0)-D/F_1;$$

$$P(2)=P(1)-D/F_2;$$

$$P(3)=P(2)-D/F_3;$$

$$P(4)=P(3)-D/F_4; \text{ and}$$

$$P(5)=P(4)-D/F_5;$$

where:
R, P(0) and P(6) are given;

$$D=P(0)-P(6); \text{ and}$$

$$F_1=R^0+R^1+R^2+R^3+R^4+R^5.$$

It is to be understood that, as a result of symmetry, Equations 2 to 4 may be adapted for computing the position of positioning lines on the other side of the smile of dentition (10). Furthermore, it is also to be understood that the positioning of side positioning line (0) may be either dependent or independent of the positioning of its corresponding positioning line (00) (see FIG. 4) on the other side of the smile or dentition (10). This is to account for the fact that smiles may not always be perfectly symmetrical or that an image of the patient may not always be perfectly centered.

Figure 5A:
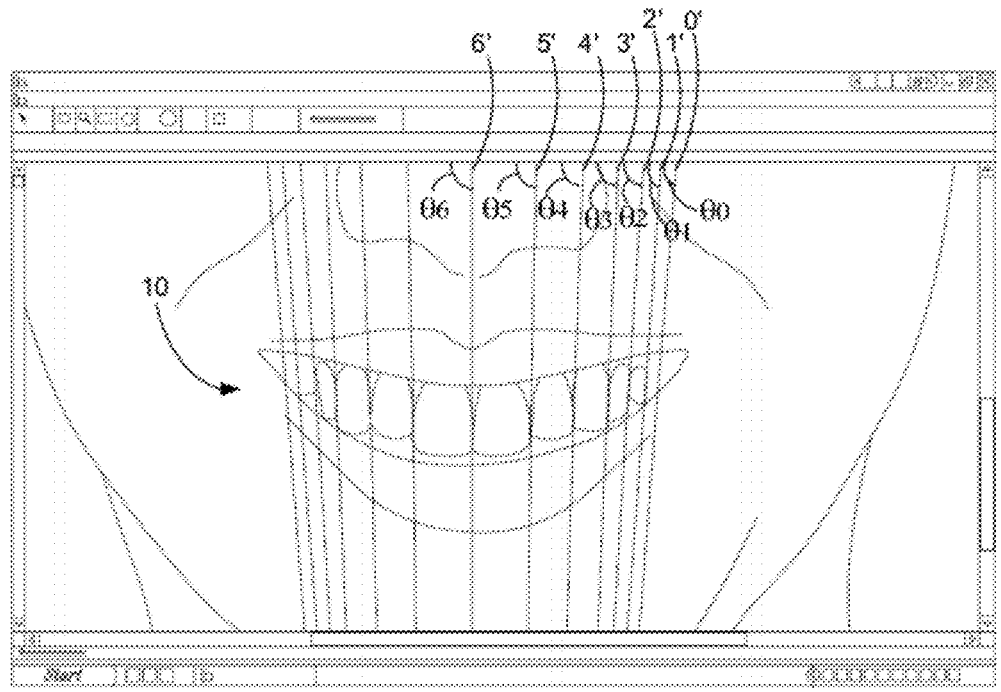
FIGS. 5A and 5B are front view of an image of the smile of an individual on which are superimposed angled positioning lines.
Figure 5B:
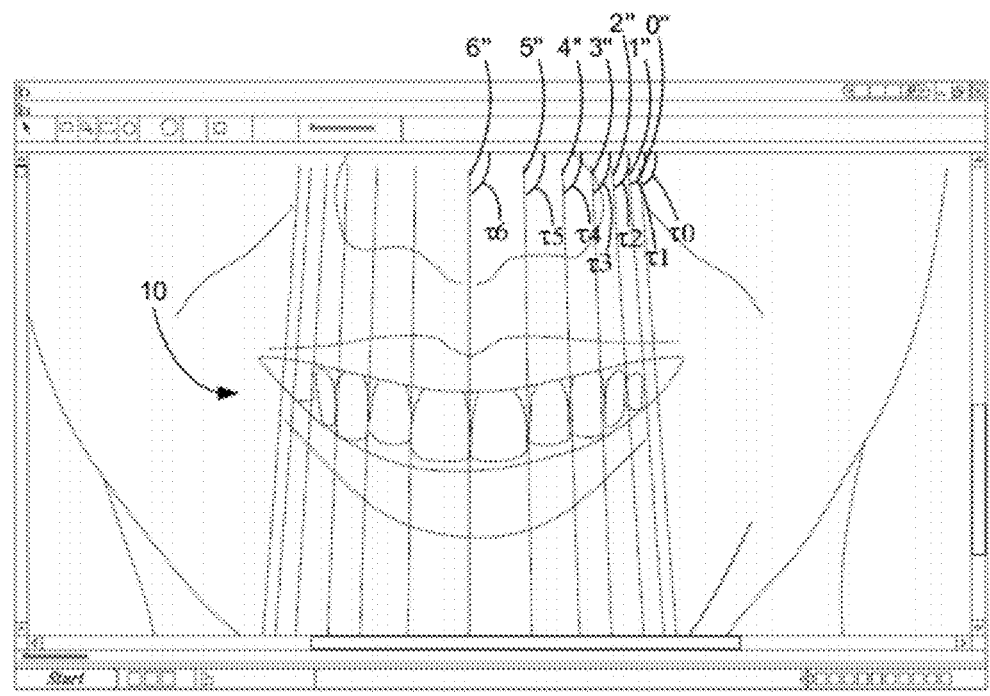

In an alternative embodiments, shown in FIGS. 5A and 5B, the positioning lines (6', 5', 4', 3', 2', 1', 0') may have corresponding angles ($\theta_6, \theta_5, \theta_4, \theta_3, \theta_2, \theta_1, \theta_0$) while positioning lines (6", 5", 4", 3", 2", 1", 0") may have corresponding angles ($\tau_6, \tau_5, \tau_4, \tau_3, \tau_2, \tau_1, \tau_0$) in order to better conform to the natural positioning of the teeth, to address a certain condition such as, for example, occlusion, or for aesthetical reasons. For example, angles of 0, 1.00, 2.00, 0.50, 3.75, 4.40 and 4.50 degrees may be used for angles ($\theta_6, \theta_5, \theta_4, \theta_3, \theta_2, \theta_1, \theta_0$) respectively. It is to be understood that other angles and that a combination of angles $\theta$ and $\tau$ may also be used.

Measurements

Figure 6:
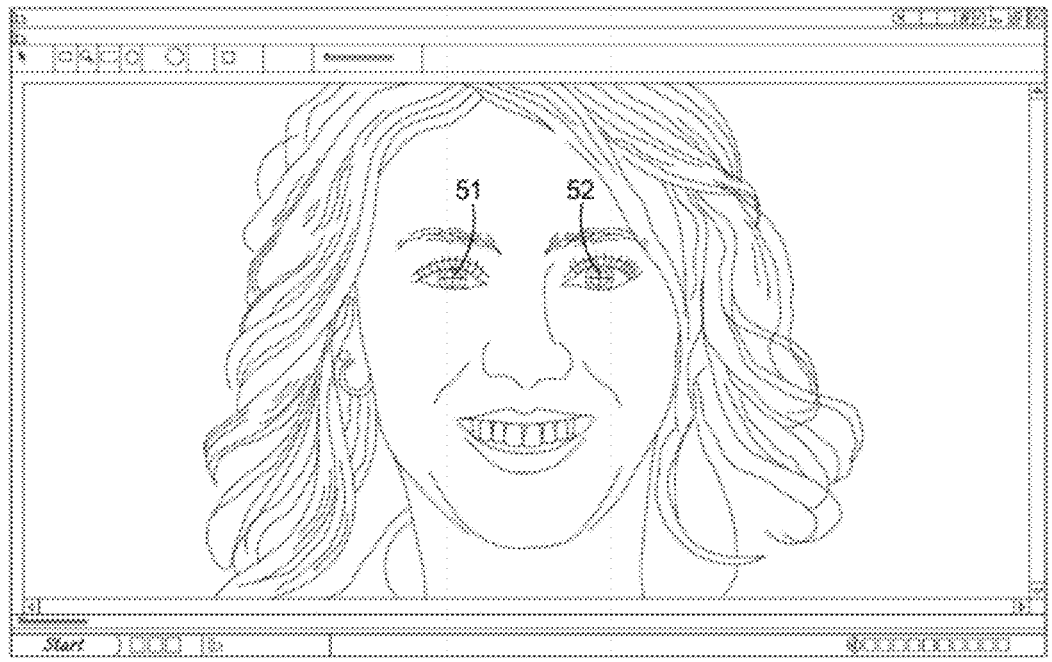
FIG. 6 is a front view image of the smile of an individual on which are superimposed two measurement reference points.
Figure 7:
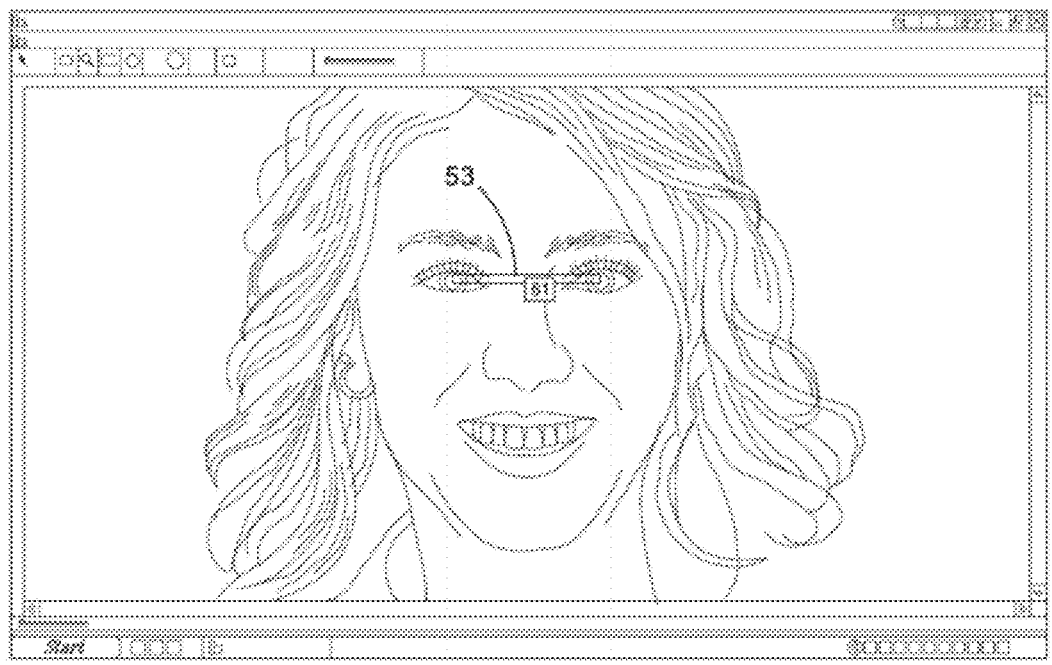
FIG. 7 is a front view image of the smile of an individual on which is superimposed a measuring rule.
Figure 8:
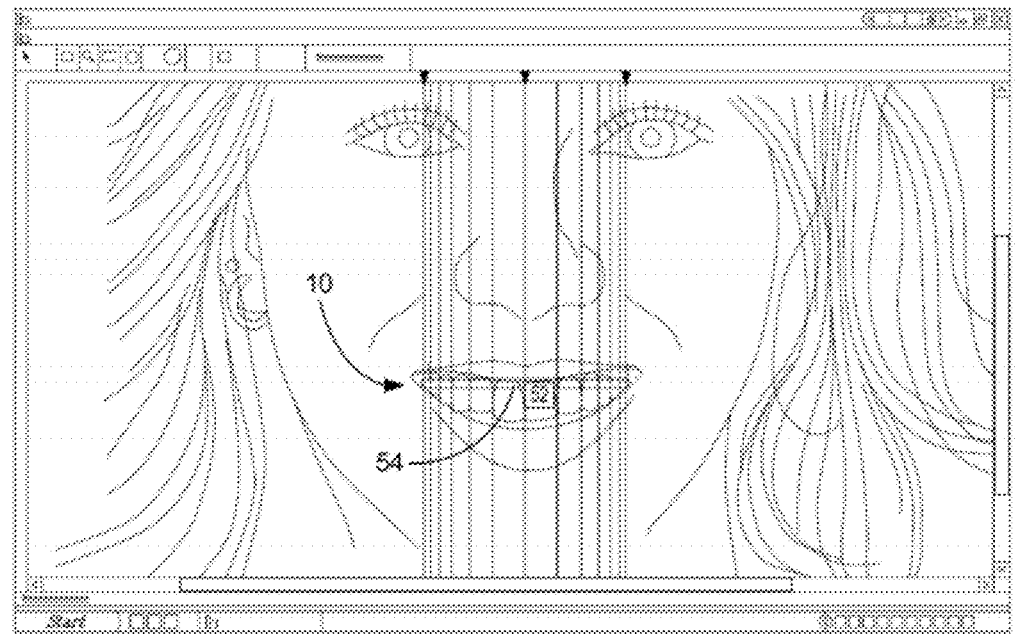
FIG. 8 is a front view image of the smile of an individual on which are superimposed positioning lines following a modified Golden Proportion with a ratio of 1:1.367 and a measuring rule.
Figure 18A:
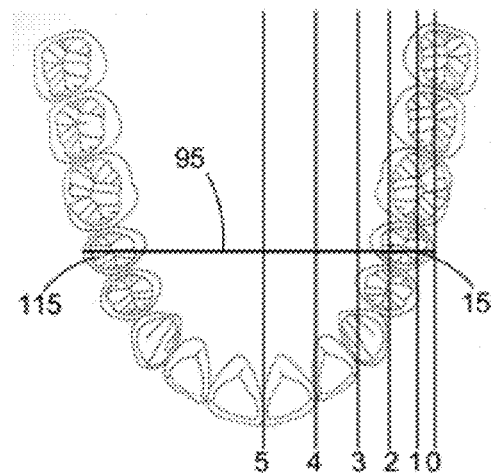
FIGS. 18A, 18B and 18C are bottom view of the upper teeth of an individual on which are superimposed positioning lines with an associated inter-molar distance.

In order to facilitate the work of the practitioner, reference points (51, 52) on the image of the patient may be identified, as shown in FIG. 6, and the distance (53) separating them inputted into the system, as shown in FIG. 7. In the example of FIGS. 6 and 7, the reference points (51, 52) are positioned at the center of the left and right pupils, respectively, and their distance (53) of 61 mm inputted as a reference. Therefore, using this reference, the measurement of various features on the image of the patient may be computed by relating the inputted distance (53) to the number of pixels between the two reference points (51, 52). For example, as shown in FIG. 8, the patient's inter-molar distance (54) may be computed using the system, in this example the inter-molar (54) being 52 mm. In this example, the inter-molar distance is the distance between the buccal faces of the left and right upper molars (see FIG. 18A for the identification of the first upper molars (116, 16).

Virtual Diagnostic Wax-Up

Figure 9:
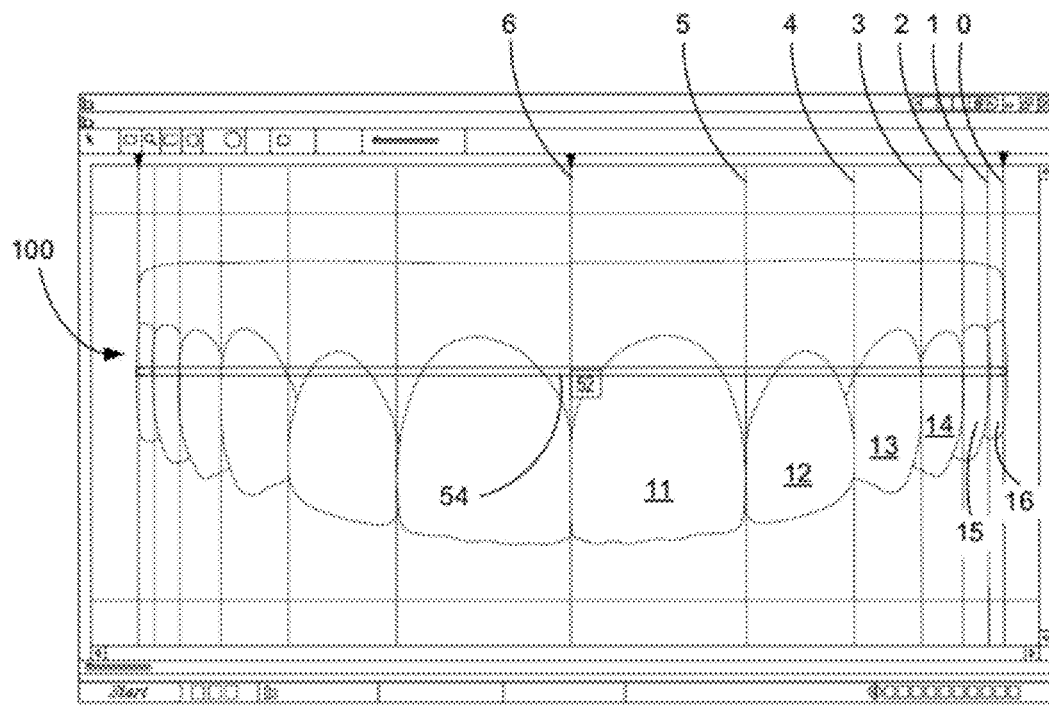
FIG. 9 is a front view image of the dentition of a virtual diagnostic wax-up on which are superimposed positioning lines following a modified Golden Proportion with a ratio of 1:1.367.
Figure 10:
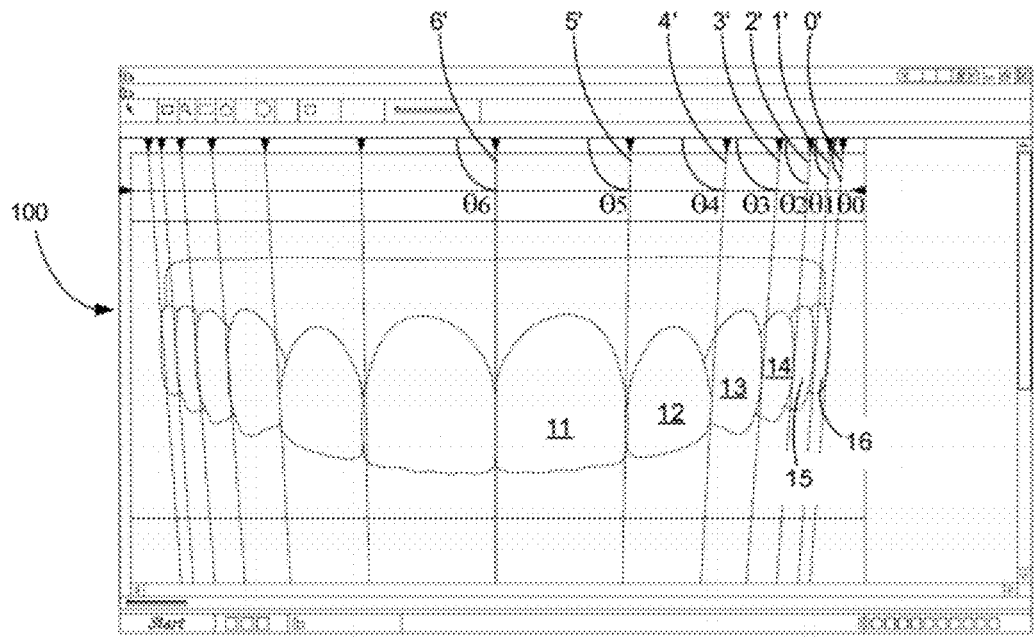
FIG. 10 is a front view image of the dentition of a virtual diagnostic wax-up on which are superimposed angled positioning lines following a modified Golden Proportion with a ratio of 1:1.367.

Referring to FIG. 9, the practitioner may use the measurements of the inter-molar distance (54) to create a virtual diagnostic wax-up (100) using the positioning lines (6, 5, 4, 3, 2, 1, 0) as guidelines as to the size and positioning of the teeth (11, 12, 13, 14, 15, 16). In an alternative embodiment, shown in FIG. 10, angled positioning lines (6', 5', 4', 3', 2', 1', 0') may also be used. It is to be understood that although not shown, angled positioning lines (6", 5", 4", 3", 2", 1", 0") as illustrated in FIG. 5B, may also be used.

The virtual diagnostic was-up (100) may then be superimposed on the image of the patient and properly scaled so as to be able to view its appearance as a replacement to the patient's dentition (10). If the practitioner wishes to make changes to the virtual diagnostic wax-up (100) he may make measurements directly on the image.

Once the practitioner is satisfied with the aesthetics of the virtual diagnostic wax-up (100), he may then use the measurements thus obtained to create a real diagnostic was-up.

It is to be understood that the virtual diagnostic wax-up (100) and the modified Golden Proportion may be included as part of a CAD CAM modeling or re-modeling software using, for example, 2D or 3D models, X-Rays or CT scans of a patient's mouth to dispose the teeth when creating, for example, ceramic teeth, orthodontic molds, dentures, etc.

Real Diagnostic Wax-Up

Figure 12:
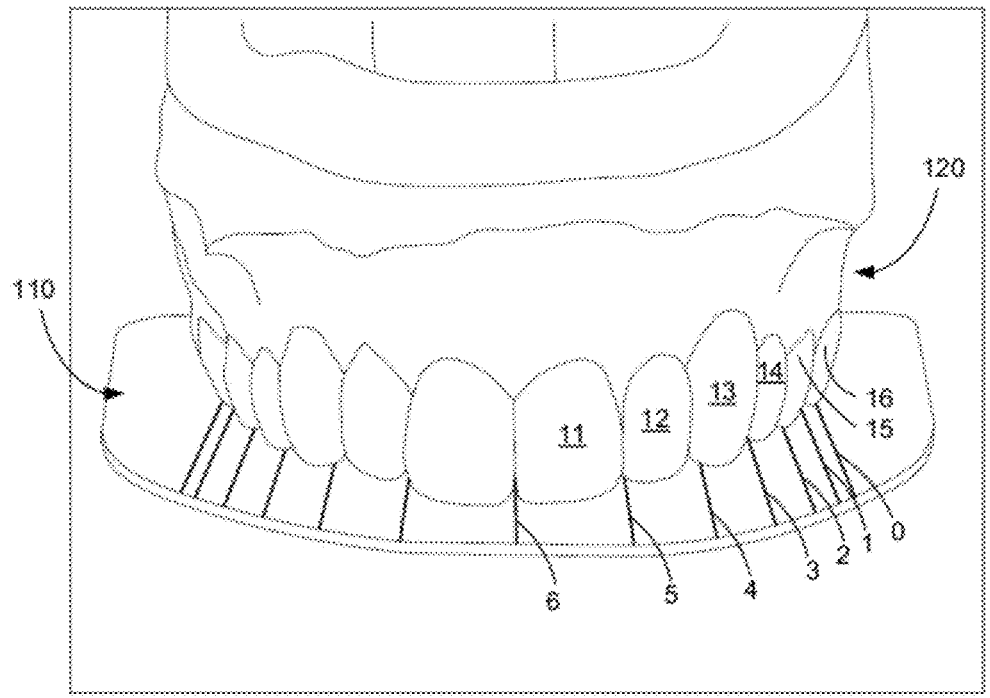
FIG. 12 is a front view image of the smile of a diagnostic was-up positioned on top of a diagnostic grid on which are superimposed positioning lines following a modified Golden Proportion with a ratio of 1:1.38.

The practitioner may use an image of the real diagnostic wax-up, such as the one shown in FIG. 12, and superimpose it on the image of the patient, properly scaled according to the inter-molar distance (54) measured on the image of the patient, in order to view the real wax-up in the patient mouth. It is to be understood that real diagnostic wax-up created by other processes, such as, for example, laboratory work, may be so viewed, not only those created from the virtual diagnostic wax-up.

Diagnostic Grid

Figure 11:
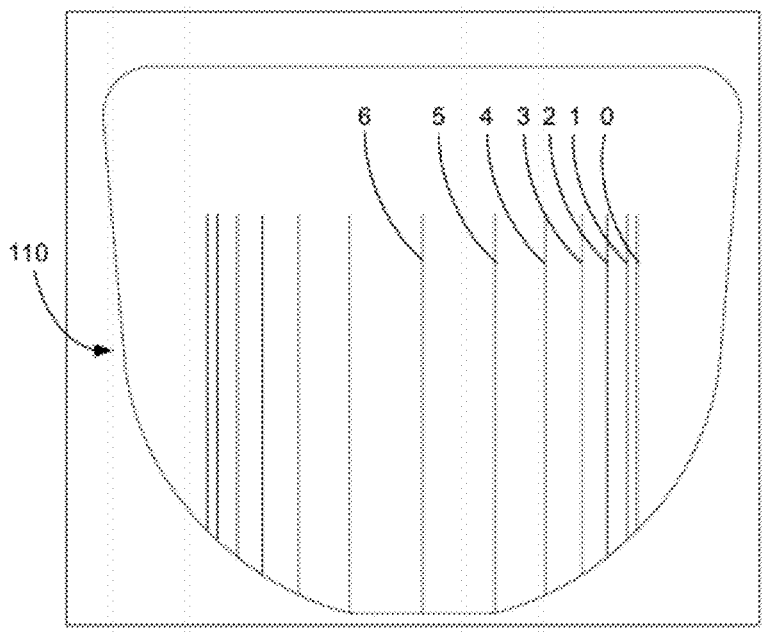
FIG. 11 is a plan view of a diagnostic grid used for laboratory work on which are superimposed positioning lines following a modified Golden Proportion with a ratio of 1:1.38.

Referring to FIG. 11, there is shown a plan view of a diagnostic grid (110) on which is applied the modified Golden Proportion (ratio of 1:1.38) with seven positioning lines, resulting in a center positioning line (6) and six side positioning lines (5, 4, 3, 2, 1, 0). The diagnostic grid (110)

may be made of a material such as, for example, plastic, paper, cardboard, plasticized, paper, metal, etc.

Referring now to FIG. 12, a diagnostic wax-up (120) may be positioned on top of the diagnostic grid (110) and the positioning lines (6, 5, 4, 3, 2, 1, 0) may be used as guidelines as to the size and positioning of the teeth (11, 12, 13, 14, 15, 16) of the diagnostic wax-up (120). The diagnostic grid (110) may also be used, for quality control, to diagnose a case, to verify a diagnostic was-up (120) created from measurements obtained from the virtual diagnostic was-up (100), from measurements obtained from the image of the patient such as shown in FIG. 8, measurements obtained directly on the patient or from model casts of his teeth.

Figure 13:
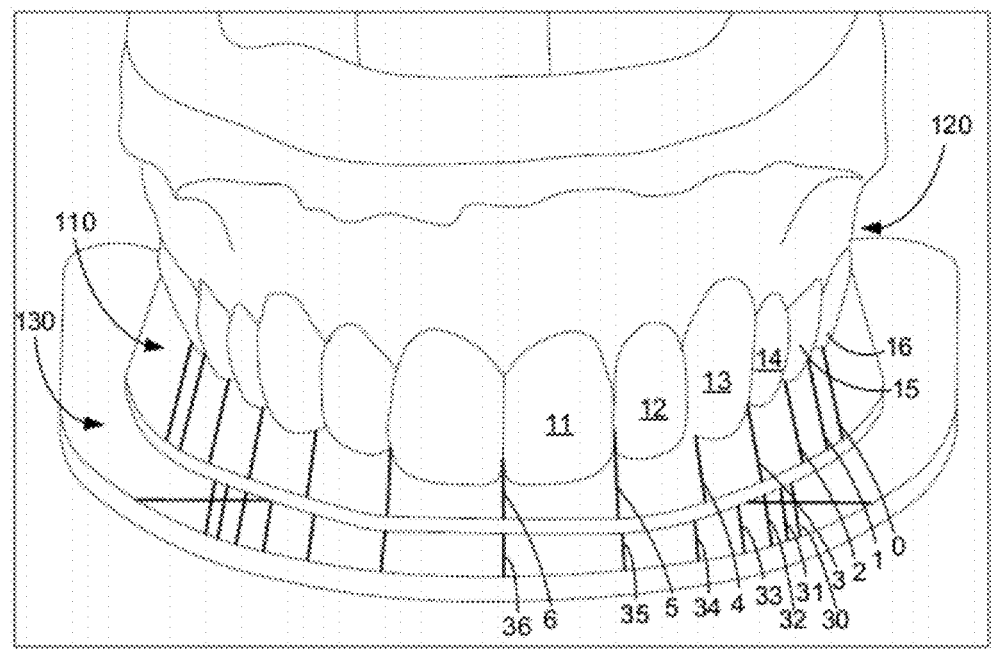
FIG. 13 is a front view image of the dentition of a diagnostic was-up positioned on top of a diagnostic grid on which are superimposed positioning lines following a modified Golden Proportion with a ratio of 1:1.38 and common diagnostic grid on which are superimposed positioning lines following a Golden Proportion with a ratio of 1:1.618.

Referring to FIG. 13, there is shown, for comparison purposes, the wax-up (120) and diagnostic grid (110) of FIG. 12, the diagnostic grid (110) following a modified Golden Proportion ratio of 1:1.38, under which is placed a conventional diagnostic grid (130) following a standard Golden Proportion ratio of 1:1.618. As it may be observed, the first three positioning lines (6, 5, 4) of diagnostic grid (110) and the first three positioning lines (36, 35, 34) of conventional diagnostic grid (130) generally correspond to the positioning of the central incisor (11) and the lateral incisor (12). However, it may also be observed that the remaining positioning lines (3, 2, 1, 0) of diagnostic grid (110) generally correspond to the positioning of the canine (13), the first premolar (14), the second premolar (15) and the first molar (16) while the remaining positioning lines (33, 32, 31, 30) of conventional diagnostic grid (130) do not at all.

Figure 14:
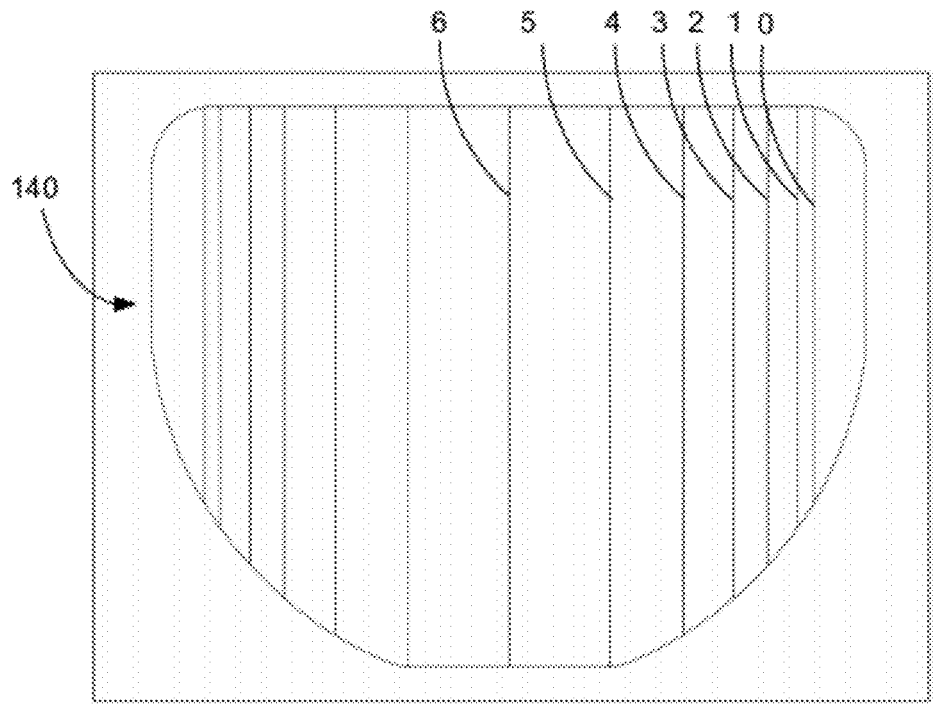
FIG. 14 is a plan view of an alternative diagnostic grid for use in an individual's mouth on which are superimposed positioning lines following a modified Golden Proportion with a ratio of 1:1.38.
Figure 15:
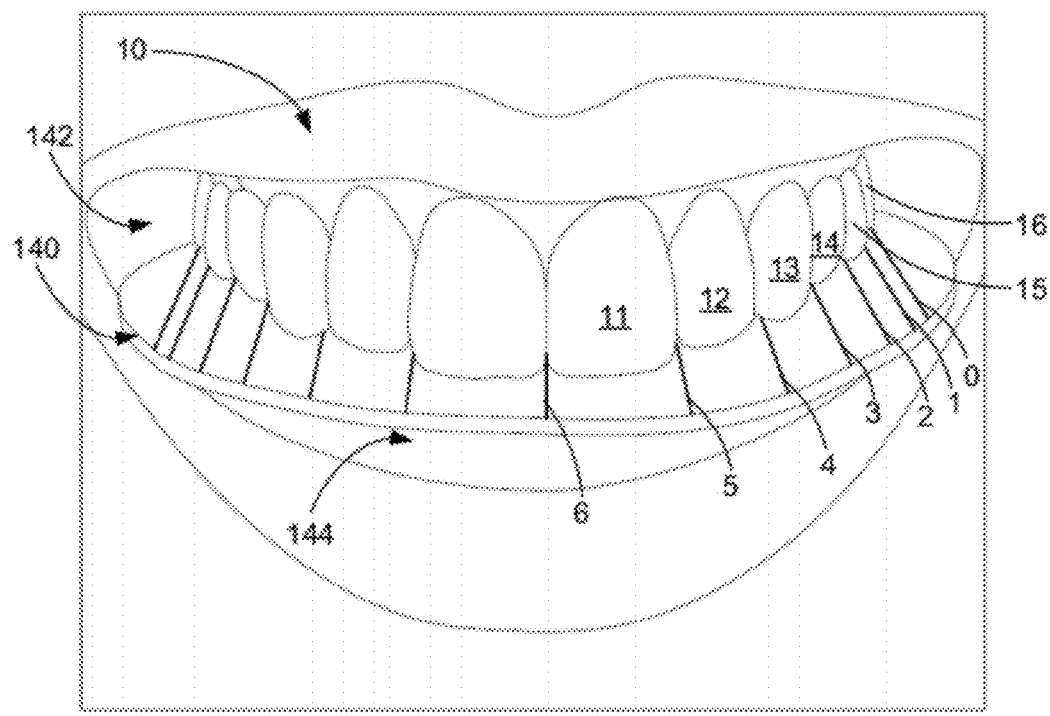
FIG. 15 is a front view image of the smile of an individual with the alternative diagnostic grid, on which are superimposed positioning lines following a modified Golden Proportion with a ratio of 1:1.38, positioned between his or her upper and lower teeth.

In an alternative embodiment shown in FIG. 14, a diagnostic grid (140), following a modified Golden Proportion ratio of 1:1.38, may have a configuration and dimensions suited for insertion in the mouth of a patient. Referring now to FIG. 15, the practitioner may position the diagnostic grid (140) between the upper (142) and lower (144) teeth of a patient and use positioning lines (6, 5, 4, 3, 2, 1, 0) as guidelines as to the positioning of the teeth (11, 12, 13, 14, 15, 16). The practitioner may then establish a diagnostic regarding the dentition (10) of the patient.

In a further alternative embodiment, the diagnostic grid (140) may have some sort of handle or protuberance at the front (not shown) so as to permit easy insertion and removal of the diagnostic grid (140) from the patient's mouth.

In typical applications the diagnostic grids (110, 140) may be created with a specific central incisor (11) width, i.e. distance between positioning lines (6) and (5), and a specific modified Golden Proportion ratio, the placement of the other positioning lines (4, 3, 2, 1, 0) being set using the selected modified Golden Proportion ratio and central incisor (11) width. For example, the width of the central incisor (11) may typically vary from 7.5 mm to 10 mm in increments of 0.5 mm and the modified Golden Proportion ratio may vary from 1:1.36 to 1:1.42 in increments or 0.01. It is understood that more precise in paper. It is understood, however, that other values may be used for the central incisor (11) as well as other modified Golden Proportion ratios as previously disclosed. It is to be understood that the above described diagnostic grids are based on the width of the central incisor (11) and a given ratio and that more precise diagnostic grids may be created by using a modified Golden Proportion calculator, which will be described further below. These more precise diagnostic grids may also be printed directly on paper, as will be seen below.

Modified Golden Proportion Gauge

Figure 16:
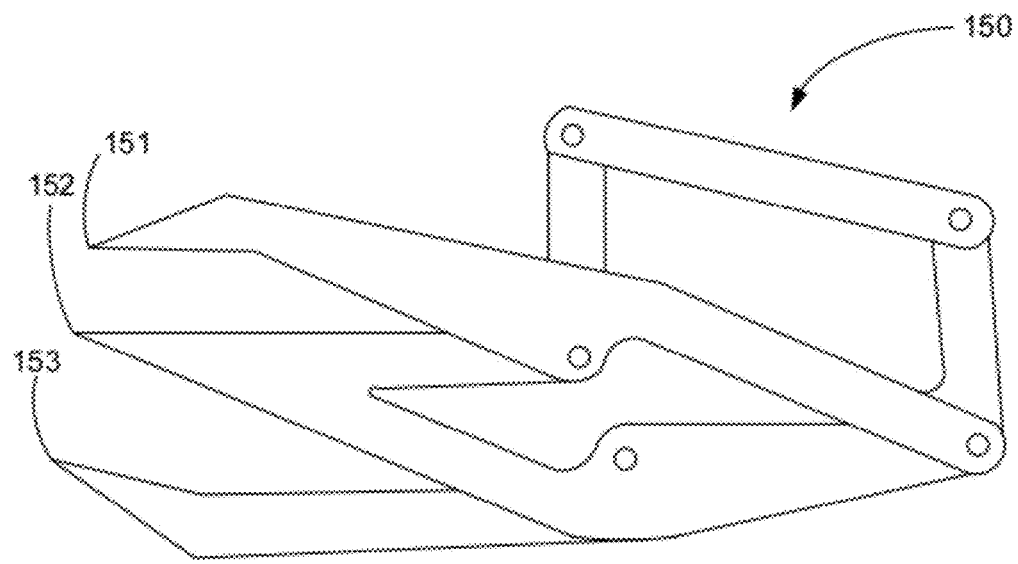
FIG. 16 is a front view illustration of a modified Golden Proportion gauge having three points mechanically following a Golden Proportion with a ratio of 1:1.38.

Referring to FIG. 16, there is shown a modified Golden Proportion gauge (150) which mechanically follows a modified Golden Proportion ratio of 1:1.38 with two points, resulting in a center point (151) and two side points (152, 153). The modified Golden Proportion gauge (150) may be made of a material such as, for example, plastic or metal. It is to be understood, however, that the modified Golden Proportion gauge (150) may follow other modified Golden Proportion ratios as previously disclosed. In an alternate embodiment of the modified Golden Proportion gauge (150 may be adjustable so as to permit the selection of a desired modified Golden Proportion ratio, for example from 1:1.25 to 1:1.50 in 0.01 increments. It is to be understood that other ratio values and increments may be used as well, for example the possible selection of modified Golden Proportion ratio may be from 1:1.20 up to 1:1.618.

Figure 17:
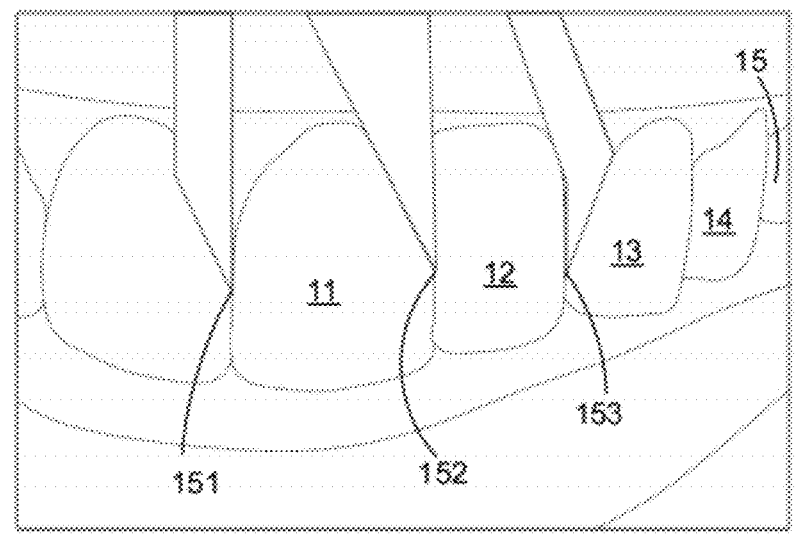
FIG. 17 is affront view image of the dentition of an individual to which is applied a modified Golden Proportion gauge having three points mechanically following a modified Golden Proportion with a ratio of 1:1.367.

Referring now to FIG. 17, the practitioner may position the center point (151) and the first side point (152) on each side of the central incisor (11) of a patient, either directly on the patient's smile or on a photograph of the patient's smile, and use the second side point (153) as a guideline as to the size and positioning of the lateral incisor (12). It is to be understood that the same process may be used on the lateral incisor (12) to obtain a guideline as to the size and positioning of the canine (13), and similarly for the first premolar (14), the second premolar (15) and the first molar (16) (not shown). It is also to be understood that in an alternative embodiment the modified Golden Proportion gauge (150) may have more than three points.

Modified Golden Proportion Calculator

As previously mentioned, the modified Golden Proportion may be included as part of a modeling and/or re-modeling software or system using, for example, 2D or 3D models, images, X-Rays or CT scans of a patient's mouth to dispose the teeth when creating, for example, ceramic teeth, orthodontic molds, dentures, etc.

To this end, with reference to FIG. 4, Equations 2, 3 and 4 may be adapted and incorporated into a modeling and/or re-modeling software or system to calculate the position of side positioning lines (5, 4, 3, 2, 1, 0) from information inputted by the user of the software or system and position them onto a 2D or 3D model, image, X-Ray or CT scan of a patient's mouth, or even print them on some supporting media. In particular, the position of the side positioning lines (5, 4, 3, 2, 1, 0) may be computed from inputting at least two quantities such as, for example, a ratio, i.e. modified Golden Proportion ratio, an inter-molar distance and a central incisor width. The various quantities may be inputted either from a user interface, such as, for example, a keyboard, a configuration file, by dragging and positioning the positioning lines (6, 5, 4, 3, 2, 1, 0) or by using some software tool or interface.

The molars used for the measurement of the inter-molar distance may vary depending on the number of positioning lines used, i.e. depending on the number of teeth may be seen in the smile of the patient. For example, referring to FIGS. 18A, 18B and 18C, in the case where six positioning lines (5, 4, 3, 2, 1, 0) are used (FIG. 18A) the inter-molar distance (95) is taken between the two second premolars (15, 115), in the case where seven positioning lines (6, 5, 4, 3, 2, 1, 0) are used (FIG. 18B), the inter-molar distance (96) is taken between the two first molars (16, 116) and in the case where eight positioning lines (7, 6, 5, 4, 3, 2, 1, 0) are used (FIG. 18C), the inter-molar distance (97) is taken between the two second molars (17, 117). In another example (not shown), four or five positioning lines may be used, in which case the inter-molar distance would be taken between the canine and first premolars, respectively.

Figure 18B:
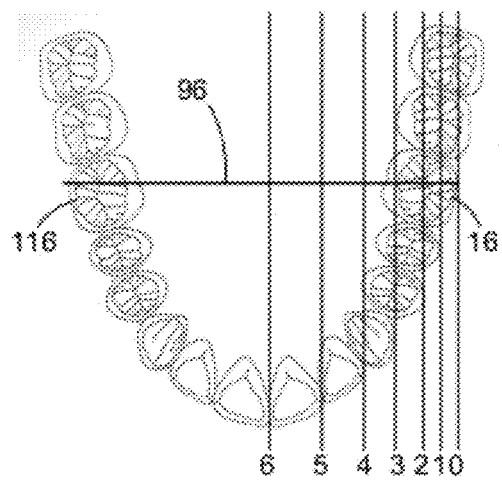
Figure 18C:
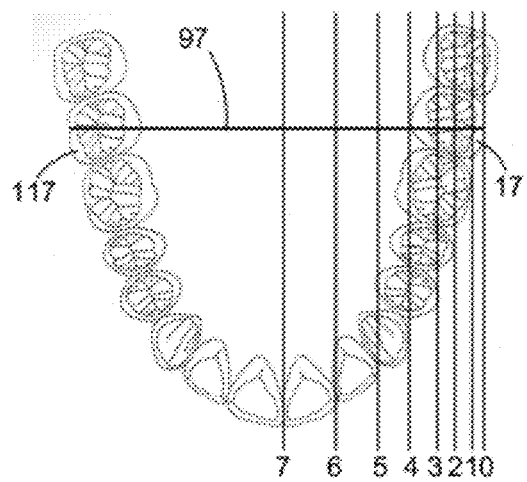

It is to be noted, however, that although reference will be made to FIG. 18B, in which there are seven positioning lines (6, 5, 4, 3, 2, 1, 0), this is for illustrative purpose only and the following discussion may similarly apply to other numbers of positioning lines. Accordingly, for the sake of clarity, the discussion will focus on the use of seven positioning lines (6, 5, 4, 3, 2, 1, 0) while the procedures will be presented such as to be applicable to varying numbers of positioning lines.

In a first non-restrictive embodiment, the position of the side positioning lines (5, 4, 3, 2, 1, 0), referred to as LinePosition(i) where I is the numeral identifying the positioning line, may be calculated from inputting a modified Golden Proportion ratio, referred to as Ratio, and an inter-molar distance (96), referred to as InterMolarDistance and applying the procedure 'CentralIncisorWidth'. It is to be understood that in the example of FIG. 18B with seven positioning lines, the variable #Of Lines, which represents the number of positioning lines, will be equal to seven. As for the inter-molar distance (96), it will be measured between the two second molars (16,116). It should be noted that in addition to calculating the position of the side positioning lines (5, 4, 3, 2, 1, 0), the procedure also provides the central incisor width.

Calculate Central Incisor Width

```
CentralIncisorWidth (Ratio, #OfLines,InterMolarDistance)
    LinePosition (#OfLines – 1) = InterMolarDistance / 2
    LinePosition (0) = 0
    Constant (1) = GetFirstPhi (Ratio, #OfLines – 2)
    For I = 2 to #OfLines – 2
        Constant (i) = Constant (i-1) / Ratio
    Next i
    For I = 1 to #OfLines – 2
        LinePosition (i) = (LinePosition (#OfLines – 1) –
                LinePosition (0)) / Cnstant (i) –
                LinePosition (i-1)
    Next i
    CentralIncisorWidth = LinePosition (i-1) – Line Position (i-2)
    RETURN CentralIncisorWidth
GetFirstPhi (Ratio, #OfLines – 2)
    For n=1 to #OfLines – 2
        GetFirstPhi = GetFirstPhi + (Ratio ^ n)
    Next n
    GetFirstPhi = GetFirstPhi + 1
    RETURN GetFirstPhi
```

In a second non-restrictive embodiment, the position of the side positioning lines (5, 4, 3, 2, 1, 0) referred to as LinePosition(i) where I is the numeral of the positioning line, may be calculating from inputting a modified Golden Proportion ratio, referred to as Ratio, and a central incisor (11) width, referred to as CentralIncisorWidth, and applying the procedure 'InterMolarDistance'. It is to be understood that in the example of FIG. 18B with seven positioning lines, the variable #OfLines, which represents the number of positioning lines, will be equal to seven. It should be noted that in addition to calculating the position of side positioning lines (5, 4, 3, 2, 1, 0), the procedure also provides the inter-molar distance (96), which is the distance between the two second molars (16,116).

Calculate Inter-Molar Distance

```
InterMolarDistance (Ratio, #OfLines, CentralIncisorWidth)
    LinePosition (#OfLines – 1) = 0
    LinePosition (#OfLines – 2) = LinePosition(#OfLines – 1) –
            CentralIncisorWidth
    Calc( )
    For i= #OfLines – 1 to 0 step –1
        LinePosition(i) = LinePosition(i) – LinePosition(0)
    Next i
    InterMolarDistance = LinePosition (#OfLines – 1) *2
    RETURN InterMolarDistance
Calc( )
```

```
    For i=#OfLines – 1 to 2 step – 1
        LinePosition(i-2) = LinePosition (i-1) – (LinePosition(i) –
                LinePositionli-1))/Ratio
    Next i
```

In a third non-restrictive embodiment, the position of the side positioning lines (5, 4, 3, 2, 1, 0) referred to as LinePosition (i) where i is the numeral of the positioning line, may be calculated from inputting a central incisor (11) width, referred to as CentralIncisorWidth, and an inter-molar distance (97), referred to as InterMolarDistance, and applying the procedure 'Ratio'. It is to be understood that in the example of FIG. 18B with seven positioning lines, the variable #OfLines, which represents the number of positioning lines, will be equal to seven. It should be noted that in addition to calculating the position of the side positioning lines (5, 4, 3, 2, 1, 0), the procedure also provides the corresponding Golden Proportion ratio.

Calculate Ratio

```
Ratio (InterMolarDistance, #OfLines, CentralIncisorWidth)
    LinePosition(#OfLines – 1) = InterMolarDistance 2
    LinePosition (#Of Lines –2) = LinePosition (#Of Lines – 1) –
            CentralIncisorWidth
    Ratio = 1
    Calc( )
    p = ratio 2
    For n = 1 to 100
        If LinePosition (0) <0 Then
            Ratio = Ratio + p
        Else
            Ratio = Ratio – p
        End if
        Calc ( )
        p = p / 2
    Next n
    RETURN Ratio
```

It is to be understood that in the loop 'For n=1 to 100', during the calculation of the modified Golden Proportion ratio, the number of times the loop is executed, namely 100, may vary depending on the desired precision of the result and as such, the number of times the loop is executed may be more or less than 100.

Referring now to FIG. 19, there is shown a flow diagram of the modified Golden Proportion calculator process. The steps composing the process are indicated by blocks 302 to 310.

The process starts at block 302, where a visual representation of the dentition is provided. Then, at block 304, a value representative of the number of teeth on a side of the dentition is inputted, this value will be used to determine the number of positioning lines, i.e. number of teeth plus one, and between which teeth the inter-molar distance is to be measured.

At block 308, at least two quantities taken from a group consisting of a ratio, an inter molar distance (also referred to as inter-teeth distance because, depending on the value inputted at block 304, the measurement may not necessarily be taken between molars as explained previously) and a central incisor width are inputted.

At block 308, the process computes the position of the positioning lines, which are used to determine the position of the teeth within the dentition, by applying a mathematical function to the value representative of the number of teeth inputted at block 304 and the quantities inputted at block 306. The mathematical function will be further detailed below.

Finally, at block 310, the positioning lines computed at block 308 are juxtaposed over the visual representation of the dentition.

Figure 20:
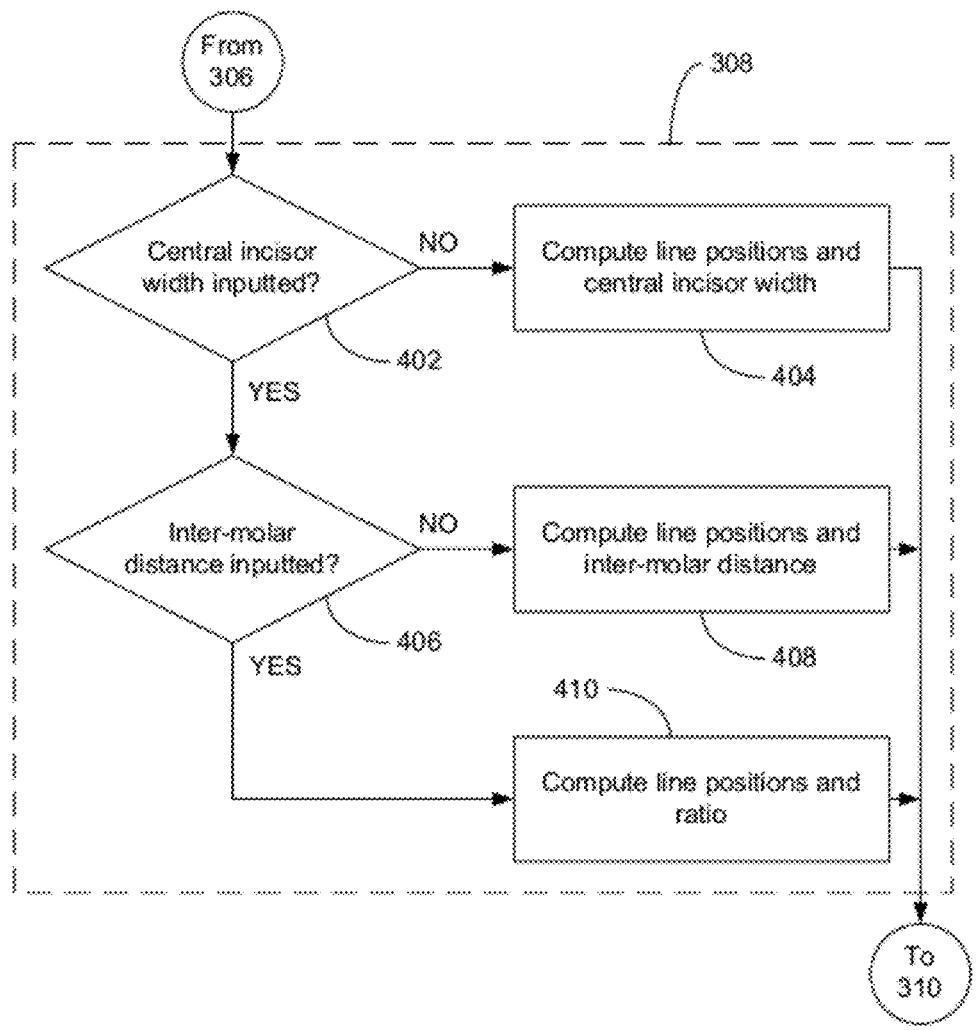
FIG. 20 is a flow diagram depicting teeth position computing step of the modified Golden Proportion calculator process of FIG. 19.

Referring to FIG. 20, there is shown flow diagram depicting teeth position computing of block 308 of the modified Golden Proportion calculator process described above. The steps composing the process are indicated by blocks 402 to 410.

At block 40, the process verifies if a central incisor width was inputted. If a central incisor width was not inputted, the process executes, at block 404, the CentralIncisorWidth procedure and then proceeds to block 310 of FIG. 19. If a central incisor width was inputted, the process proceeds to block 406.

At block 406, the process verifies if an inter-molar distance was inputted. If an inter-molar distance was not inputted, the process executes, at block 408, the InterMolarDistance procedure and then proceeds to block 310 of FIG. 19. If an inter-molar distance was inputted, the process proceeds to block 410.

At block 410, the process executes the Ratio procedure and then proceeds to block 310 of FIG. 19.

Figure 21:
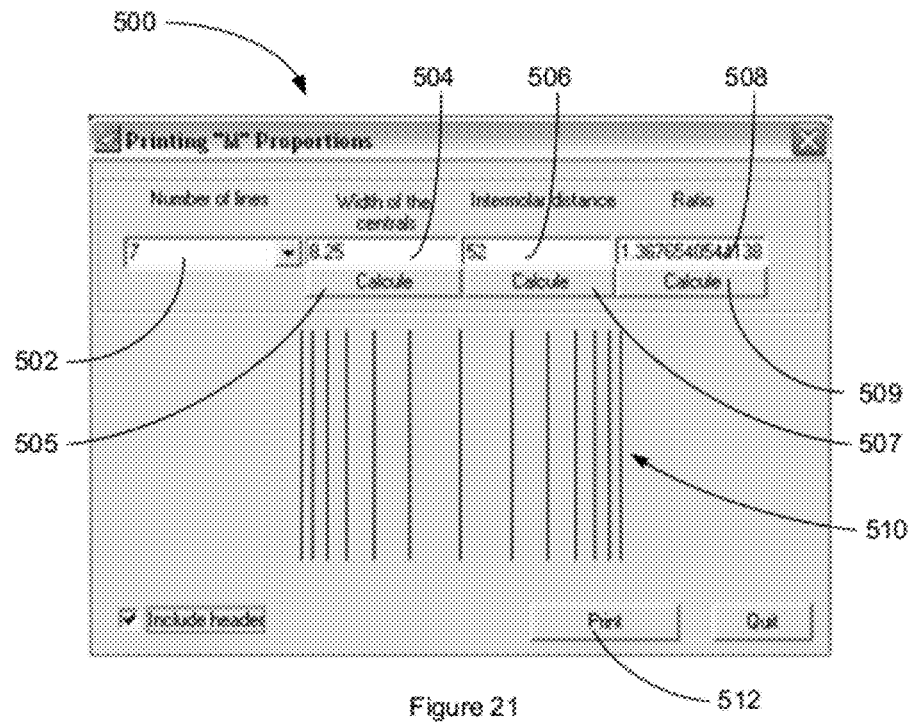
FIG. 21 is an example of a modified Golden Proportion calculator interface.

Referring to FIG. 21, there is shown an example of an interface (500) that may be used with the modified Golden Proportion calculator. A first (502), second (504), third (506) and fourth (508) input boxes may be used to enter the number of lines to be displayed (#OfLines), the central incisor width (CentralIncisorWidth), the inter-molar distance (InterMolarDistance) and the modified Golden Proportion ratio (Ratio) respectively. As discussed previously, after the number of lines has been entered in input box (502), which may also be in the form of a scroll down menu, at least two of input boxes (504), (506) and (508) must be filled, i.e. two out of the central incisor width, inter-molar distance and modified Golden Proportion ratio must be entered.

To activate the modified Golden Proportion calculator, the activation buttons (505), (507) and (509) corresponding the missing quantity is selected. For example, if the central incisor width (504) and inter-molar distance (506) are entered, then activation button (509) is selected. The modified Golden Proportion calculator will then use the Ratio procedure to calculate the position of the side positioning lines (5, 4, 3, 2, 1, 0) as well as the Modified Golden Proportion ratio, which is then displayed in input box (208). It is to be understood that procedures CentralIncisorWidth and InterMolarDistance are similarly used when activation buttons (505) and (507) are selected, respectively.

Figure 22:
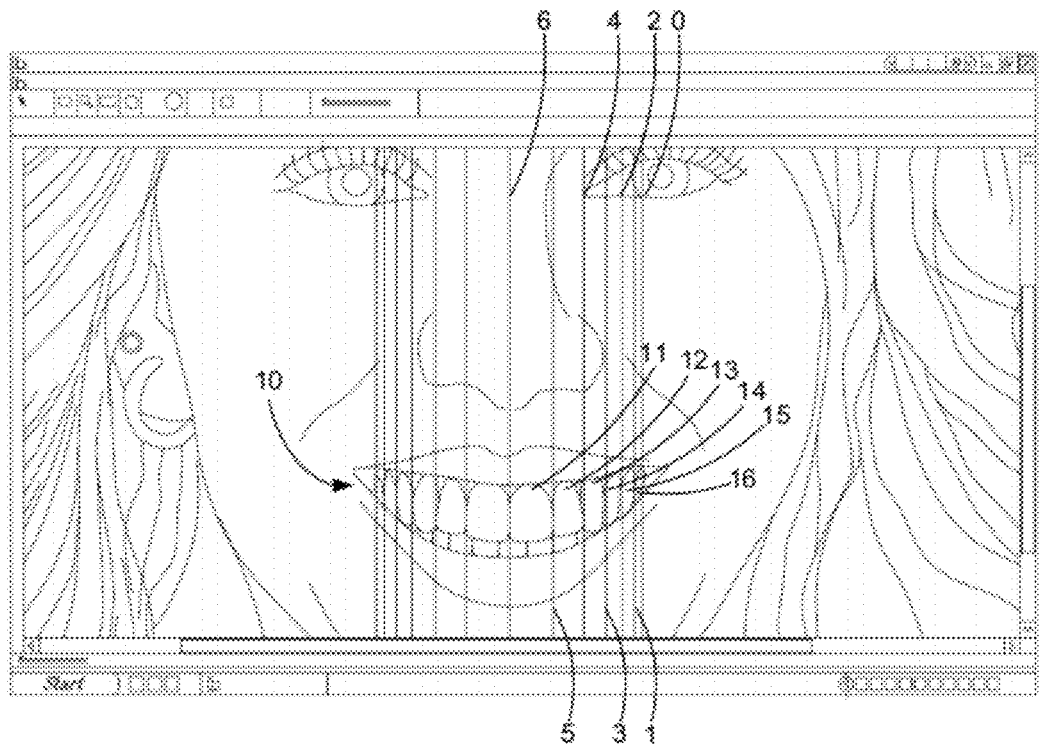
FIG. 22 is a front view image of the smile of an individual having received corrective crowns following the modified Golden Proportion shown in FIG. 21.

The positioning lines (6, 5, 4, 3, 2, 1, 0) may then be displayed (510) on the modified Golden Proportion calculator interface (500) and/or on an image of the patient's dentition (10), as shown in FIG. 22. Furthermore, the interface (500) may have various options such as, for example, the ability to print the positioning lines (6, 5, 4, 3, 2, 1, 0) on a sheet of paper or to create, for example, diagnostic grids such as shown in FIGS. 11 and 14, by selecting the print button (512).

Referring back to FIG. 20, there is shown an example of possible values obtained from the modified Golden Proportion calculator with seven lines (input box 502), a central incisor width of 8.25 mm (input box 504), an inter-molar distance of 52 mm (input box 506) and a modified Golden Proportion ratio of 1.3676540544138 (input box 508). The resulting positioning lines (6, 5, 4, 3, 2, 1, 0) are displayed (510) on the modified Golden Proportion calculator interface (500).

Referring now to FIG. 22, there is shown representation of a image of the dentition (10) of a patient having received corrective crowns following the modified Golden Proportion calculator values displayed in the interface (500) of FIG. 21.

It may be observed that the corrected positions of the central incisor (11), lateral incisor (12), canine (13), first premolar (14), second premolar (15) and first molar (16) are now generally in accordance with the corresponding center positioning line (6) and six side positioning lines (5, 4, 3, 2, 1, 0).

It is to be understood that the disclosed non-limitative illustrative embodiments may be used for assisting in various dental works such as, for example, surgery, fabrication and positioning of implants, fabrication of ceramic facings and crowns, fabrication of dentures, orthodontic molds, partial and complete prostheses, etc.

Although the present invention has been described by way of an illustrative embodiment and example thereof, it should be noted that it will be apparent to persons skilled in the art that modifications may be applied to the present particular embodiment without departing from the scope of the present invention.

What is claimed is:

1. A method for designing an improved dentition of a patient, comprising the steps of:
 a) inputting a value representative of a number of visible teeth on each side of the patient's actual dentition;
 b) inputting a value representative of an inter-molar distance of the patient's actual dentition and a value representative of the patient's actual central incisor width; and
 c) computing position of teeth of the improved dentition by applying a bilateral mathematical function to the value representative of the number of visible teeth on each side of the dentition, the value representative of the central incisor width and the value representative of the actual inter-molar distance;
 wherein the bilateral mathematical function is based on a modified Golden Proportion with a variable ratio of 1:1.367 in a range between 1:1.200 and 1:1.618.

2. A method according to claim 1, wherein the value representative of the number of visible teeth on each side of the dentition is a number between 3 and 8.

3. A method according to claim 1, wherein the position of the teeth of the improved dentition is a measure of a visible width of each teeth as seen from a frontal two-dimensional view.

4. A method according to claim 1, further comprising displaying positioning lines defining the computed position of the teeth.

5. A method according to claim 1, further comprising printing positioning lines defining the computed position of the teeth.

6. A method for designing an improved dentition of a patient, comprising the steps of:
 a) providing a visual representation of the patient's actual dentition;
 b) inputting a value representative of a number of visible teeth on a side of the patient's actual dentition;
 c) inputting a value representative of an inter-molar distance of the patient's actual dentition and a value representative of a central incisor width of the patient's actual dentition;
 d) computing position of the teeth of the improved dentition by applying a bilateral mathematical function to the value representative of the number of visible teeth on a side of the dentition, the value representative of the inter-molar distance and the value representative of the central incisor width; and
 e) juxtaposing positioning lines over the visual representation of the patient's actual dentition, the positioning lines indicating the position of the teeth of the improved dentition as computed in step d);

wherein the bilateral mathematical function is based on a modified Golden Proportion with a variable ratio of 1:1.367 in a range between 1:1.200 and 1:1.618.

7. A method according to claim 6, wherein the value representative of the number of visible teeth on a side of the dentition is a number between 3 and 8.

8. A method according to claim 6, wherein the position of the teeth of the improved dentition is a measure of a visible width of each teeth as seen from a frontal two-dimensional view.

9. A method according to claim 6, wherein the visual representation of the patient's actual dentition is taken from a group consisting of a 2D digital image of the dentition, a 3D digital image of the dentition, a digital picture of a patient's dentition, a digital image of a virtual diagnostic wax up and a digital picture of a diagnostic was up.

10. A method according to claim 6, further comprising printing the results of step e).

11. A method according to claim 6, wherein step d) also computes a missing quantity taken from a group consisting of a ratio, an inter teeth distance and a central incisor width.

12. A method according to claim 11, further comprising outputting the missing quantity.

13. A method according to claim 6, wherein the positioning lines are generally parallel to an axis defined by the length of the teeth.

14. A method according to claim 6, wherein the positioning lines are angled with respect to an axis defined by the length of the teeth.

15. A method according to claim 14, further comprising adjusting the angle of at least one of the positioning lines.

16. A system for designing an improved dentition of a patient, comprising:
    means for providing a visual representation of the patient's actual dentition;
    means for inputting a value representative of a number of visible teeth on a side of a dentition;
    means for inputting a value representative of the patient's actual inter-molar distance and a value representative of the patient's actual central incisor width;
    means for computing position of the teeth of the improved dentition by applying a bilateral mathematical function to the value representative of the number of visible teeth, the value representative of the actual central incisor width and the value representative of the actual inter-molar distance; and
    means for displaying positioning lines over the visual representation of the patient's actual dentition, the positioning lines indicating the position of the teeth as computed;
    wherein the bilateral mathematical function is based on a modified Golden Proportion with a variable ratio of 1:1.367 in a range between 1:1.200 and 1:1.618.

17. A system according to claim 16, wherein the visual representation of the patient's actual dentition is taken from a group consisting of a 2D digital image of the dentition, a 3D digital image of the dentition, a digital picture of a patient's dentition, a digital image of virtual diagnostic wax up and a digital picture of a diagnostic was up.

18. A system according to claim 16, further comprising means for printing the positioning lines.

19. A system according to claim 16, wherein the computing means computes a missing quantity taken from a group consisting of a ratio, an inter teeth distance and a central incisor width.

20. A system according to claim 19, wherein the displaying means displays the missing quantity.

21. A system according to claim 16, wherein the positioning lines are generally parallel to an axis defined by the length of the teeth.

22. A system according to claim 16, wherein the positioning lines are angled with respect to an axis defined by the length of the teeth.

23. A system according to claim 22, further comprising means for adjusting the angle of at least one of the positioning lines.

* * * * *

UNITED STATES PATENT AND TRADEMARK OFFICE
CERTIFICATE OF CORRECTION

PATENT NO. : 8,423,335 B2
APPLICATION NO. : 13/267615
DATED : April 16, 2013
INVENTOR(S) : Alain Methot It is certified that error appears in the above-identified patent and that said Letters Patent is hereby corrected as shown below:

In the Specification

Column 2, lines 62-63, "diagnostic was-up" should read -- diagnostic wax-up --.

Column 2, lines 66-67, "diagnostic was-up" should read -- diagnostic wax-up --.

Column 4, line 37, "Application of the Golden Proportion" should read -- Application of the Modified Golden Proportion --.

Column 6, line 37, "diagnostic was-up" should read -- diagnostic wax-up --.

Column 6, line 45, "diagnostic was-up" should read -- diagnostic wax-up --.

Column 7, line 9, "diagnostic was-up" should read -- diagnostic wax-up --.

Column 7, line 10, "diagnostic was-up" should read -- diagnostic wax-up --.

In the Claims

Claim 1, column 12, lines 35-36, "a variable ratio of 1:1.367 in a range between 1:1.200 and 1:1.618" should read -- a variable ratio in a range between 1:1.200 and 1:1.618 --.

Claim 6, column 13, lines 4-5, "a variable ratio of 1:1.367 in a range between 1:1.200 and 1:1.618" should read -- a variable ratio in a range between 1:1.200 and 1:1.618 --.

Claim 9, column 13, line 18, "diagnostic was up" should read -- diagnostic wax up --.

Signed and Sealed this
Eighteenth Day of August, 2015

Michelle K. Lee
*Director of the United States Patent and Trademark Office*

CERTIFICATE OF CORRECTION (continued)
U.S. Pat. No. 8,423,335 B2

Claim 16, column 14, lines 15-16, "a variable ratio of 1:1.367 in a range between 1:1.200 and 1:1.618" should read -- a variable ratio in a range between 1:1.200 and 1:1.618 --.

Claim 17, column 14, line 22, "diagnostic was up" should lead -- diagnostic wax up --.